United States Patent [19]

Papazian

[11] Patent Number: 5,297,435
[45] Date of Patent: Mar. 29, 1994

[54] RESIDUAL STRESS MEASUREMENT AT FASTENER HOLES

[76] Inventor: John M. Papazian, 255-20 West End Dr., Great Neck, N.Y. 10020

[21] Appl. No.: 873,760

[22] Filed: Apr. 27, 1992

[51] Int. Cl.⁵ .............................................. G01N 29/18
[52] U.S. Cl. ........................................ 73/597; 29/407; 29/705
[58] Field of Search ................. 73/597, 598, 801, 802; 29/407, 705

[56] References Cited

U.S. PATENT DOCUMENTS

| | | | |
|---|---|---|---|
| 4,363,242 | 12/1982 | Heyman | 73/597 |
| 4,953,973 | 9/1990 | Leftheris et al. | 73/800 |
| 5,176,033 | 1/1993 | Jones et al. | 73/597 |

*Primary Examiner*—John E. Chapman
*Attorney, Agent, or Firm*—Pollock, Vande Sande & Priddy

[57] ABSTRACT

A system is employed for measuring the changes in velocity of ultrasonic waves in structural members as a result of variations in local elastic stresses about fastener holes. In a first embodiment, piezoelectric transducer and detector members are employed while in a second embodiment non-contacting laser transducer and detector components are used. The invention is capable of detecting the establishment of optimum cold working around a fastener hole by monitoring the velocity of ultrasonic waves in the structural material. This ensures maximized useful life of the structural member by avoiding over or under worked fastener holes.

10 Claims, 1 Drawing Sheet

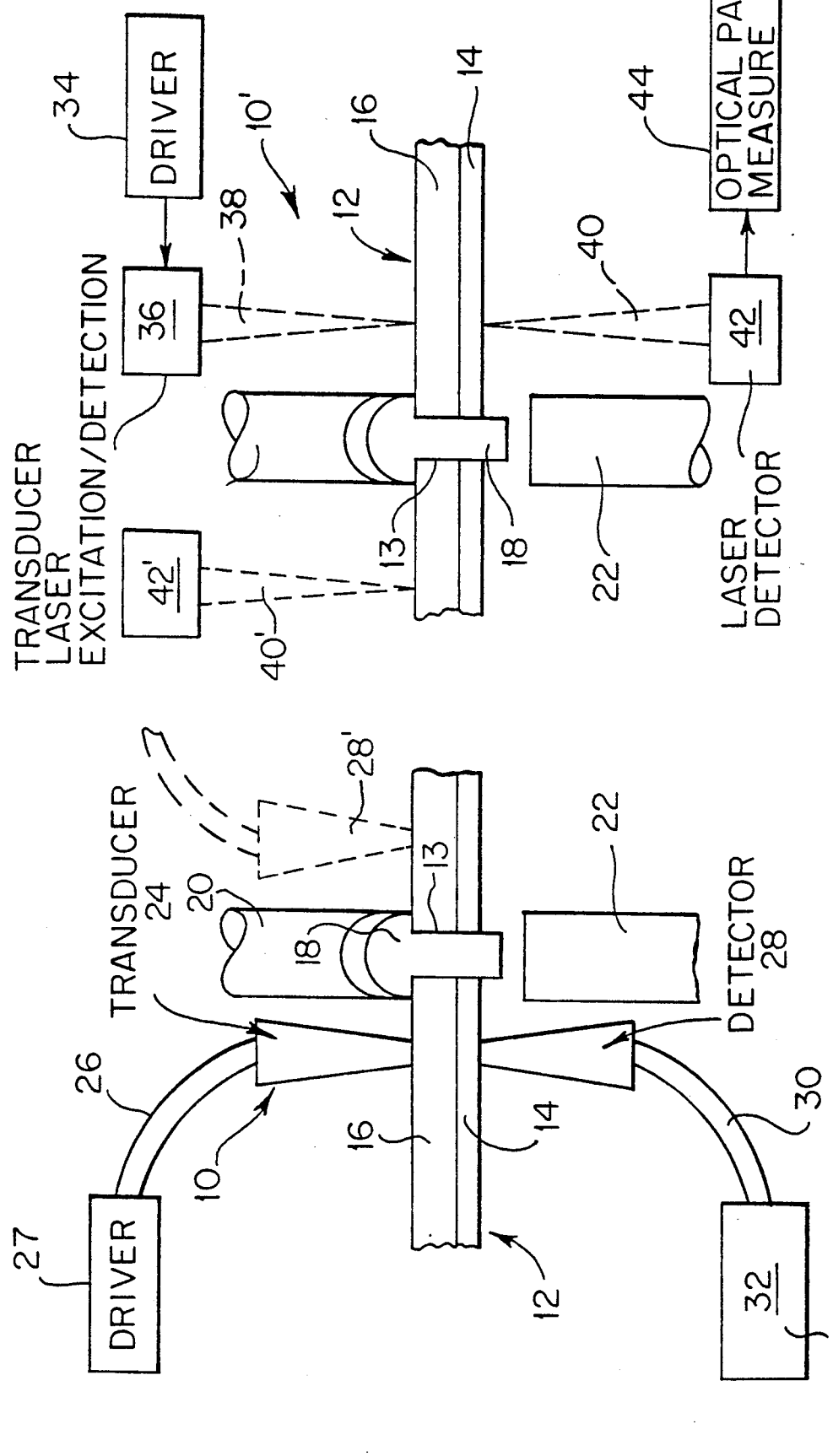

RESIDUAL STRESS MEASUREMENT AT FASTENER HOLES

FIELD OF THE INVENTION

The present invention relates to an ultrasonic measurement system, and more particularly to such a system for measuring the presence and magnitude of local elastic stresses in metal.

BACKGROUND OF THE INVENTION

The lives of aerospace structures, such as aircraft, are limited by fatigue cracking. Fatigue cracks usually begin at holes in the structure. Holes are necessary in order to join together the various components of the structure. Several techniques exist for improving the fatigue life of holes; these techniques often involve the introduction of compressive residual stresses in a circumferential (hoop) direction around the hole. These compressive stresses counteract the tensile stresses imposed by the structure and lead to a lower net tensile stress in the region. Tensile stresses are required to start and propagate a fatigue crack, so the introduction of beneficial residual compressive stresses results in a significant increase in the fatigue life of the structure.

There are various techniques for the introduction of beneficial residual stresses around holes. Some of the common techniques include cold working of the hole before fastener installation, the installation of interference fit fasteners, or the installation of oversqueezed rivets. Cold working before fastening often involves expansion of the hole by passage through the hole of an oversized mandrel, with or without a sleeve to protect the inside diameter. The cold working associated with the passage of the oversize mandrel results in the introduction of beneficial residual compressive stresses. A difficulty with this technique is the inability of the operator to accurately control the amount of cold working, and hence the amount of residual stress. The amount of cold working is determined by the relative sizes of the initial inside diameter of the hole and the outside diameter of the mandrel. Normal machining tolerances on these diameters leads to a variability in the amount of cold work in nominally similar situations. In addition, it is difficult to determine if the proper amount of expansion and residual stress has been introduced unless the initial and final diameters of the holes are accurately measured.

With interference fit fasteners, a fastener whose outside diameter is greater than the inside diameter of the hole is forced into the hole, thereby expanding it and introducing beneficial residual stresses. In this case, it is again difficult to determine if the proper amount of beneficial residual stress has been introduced around the hole.

Likewise, with oversqueezed rivets, the rivet is placed in the hole, then the tail of the rivet is mechanically upset in order to clinch the rivet in place, and an additional amount of force is applied in order to "oversqueeze" the rivet, causing its diameter to increase, expand into the hole, and introduce beneficial residual stresses in the material surrounding the hole. In this operation, it is impossible to determine if the proper amount of "oversqueeze" has been introduced. Current practice usually requires that five rivets be "oversqueezed" in dummy samples before and after actual riveting on the structure. The dummy samples are cut apart and destructively examined to determine if the correct force setting had been applied by the machine. If the sample rivets are good, it is assumed that the rivets in the structure are also good. If they are bad, then all of the intervening rivets must be removed and re-installed. Even if the dummy rivets were good, there is no way to determine if intermittent problems with the machine or variation in the hole or rivet diameters caused a variation in the amount of oversqueeze and hence beneficial residual stress in the actual part. If only one hole of the thousands that exist in a typical structure is improperly prepared, the structure will fail at the defective hole. The weakest link determines the life of the structure.

BRIEF DESCRIPTION OF THE PRESENT INVENTION

With the proposed invention, the amount of deformation around the hole could be measured, either after the fact or in real time. Measurement after the fact would be of use to determine if the process had been correctly performed, but measurement in real time would allow direct, real-time control of the process introducing the residual stresses. Direct control of the process, with simultaneous verification of the amount of deformation, would allow for more consistent fastening and would eliminate the need for before and after quality checks. This type of device would be ideally suited for robotic application and could significantly reduce assembly costs. The proposed invention involves real time measurement of the deformation of the material around the hole during the cold working process, during interference fit fastener installation, or during "oversqueezing" of rivets.

It is well established that the velocity of ultrasonic waves in material is affected by the presence of elastic stresses. Thus, a device that measured the ultrasonic wave propagation velocity near the hole in a structure could be used to measure the presence and magnitude of local elastic stresses. A pulse of ultrasonic waves is introduced at the top surface of the part being fastened. This pulse may be introduced by a contacting transducer or by a non-contacting device. In each case, the reflected or transmitted signal is detected by a receiving transducer on the back side of the structure or by a receiving transducer on the front side of the structure but on the opposite side of the hole. The transmitting transducer can also serve as the receiving transducer in some circumstances. Contacting transducers may be made from piezoelectric ceramic materials.

Non-contacting transducers can be pulsed lasers. The sound velocity in the region of the hole can be measured from the ultrasonic signal, and the magnitude of the stress in the region determined. The stress in a particular direction (e.g. circumferential or radial) could be determined by using polarized waves.

BRIEF DESCRIPTION OF THE FIGURES

The above-mentioned objects and advantages of the present invention will be more clearly understood when considered in conjunction with the accompanying drawings, in which:

FIG. 1A is a diagrammatic illustration of the first embodiment of the present invention wherein contacting transducer and detector components are employed;

FIG. 1B is a second embodiment of the present invention illustrating non-contacting transducer and detector components of the laser type.

DETAILED DESCRIPTION OF THE INVENTION

Referring to the figures and more particularly FIG. 1A, a first embodiment of the present invention utilizes a contact system 10 for determining local elastic stresses within a structural member 12, comprising two sheets of material 14 and 16 illustrated by way of example. The local elastic stresses are created around a hole 13 formed in the structural member 12, the hole being cold worked by a fastener, such as rivet 18 located in the hole. Cold working commences when the rivet is compressed by joint action of a backing bar 20 contacting the rivet head and a rivet tool 22 contacting the rivet tail.

In order to measure the induced local elastic stress, a conventional ultrasonic piezoelectric transducer 24 contacts the upper surface of the structural member 12 while a corresponding conventional piezoelectric detector 28 contacts the opposite surface. The detector may be positioned along the same surface as transducer 24, as indicated by the transducer 28'. An ultransonic driver 27 is connected by a wire 26 to the transducer while a wire 30 connects the detector 28 with a typical ultrasonic analyzer capable of measuring the propagation velocity of the emitted ultrasonic signal.

For a particular setup, the propagation velocity of ultrasonic waves is measured for a desirable deformation. Thus, during real time measurement, the "oversqueezing" of rivets or cold working of interference fit fasteners can be stopped when the target velocity change is measured.

A second embodiment of the present invention is generally indicated by reference numeral 10' in FIG. 1B. In the latter-mentioned system, non-contacting transducer and detector components are employed. For example, a laser driver 34 provides excitation energy to a conventional laser transducer 36 which directs pulsed energy along path 38 to a first surface of structural member 12 exciting ultrasonic waves in member 12.

As in the case of the contacting system of FIG. 1A, a detector is positioned adjacent an opposite surface of the structural member along path 40 or on the same side of the structure but on the opposite side of the hole as shown in FIG. 1B (path 40' and detector 42'). In the non-contacting embodiment of FIG. 1B, the detector 42 is of the laser type which detects optical path length changes in response to ultrasonic vibration in the structural member 12.

The laser detector 42 is of a conventional type and has its output connected to an appropriate prior art analyzer 44 which measures the propagation velocity of the ultrasonic signal in the structural member corresponding to changes in local elastic stress around the hole 13. The prior art analyzer 44 measures the characteristics of the ultrasonic signal in the structural member by measuring changes in the optical path length 40.

By virtue of the foregoing description, it will be appreciate that the present invention allows the cold working of fastener holes to be adjusted in real time to a desired extent so as to extend the fatigue life of the structural member and minimize the chance of underworking or overworking a fastener hole.

It should be understood that the invention is not limited to the exact details of construction shown and described herein for obvious modifications will occur to persons skilled in the art.

I claim:

1. A method for measuring local elastic stress at a fastener hole of a structural member comprising the steps:
   introducing ultrasonic energy into the member;
   cold working the hole;
   measuring the propagation velocity changes of the ultrasonic energy as the hole is cold worked; and
   terminating the cold working when a preselected velocity change is measured corresponding to optimum induced elastic stress in the material around the hole.

2. The method set forth in claim 1 wherein the ultrasonic energy is introduced by direct contact with a vibrating element.

3. The method set forth in claim 1 wherein the ultrasonic energy is introduced by a pulsed beam of coherent light directed toward a surface of the structural member.

4. The method set forth in claim 2 wherein the propagation velocity change measurement is made by direct contact velocity detection at the surface of the structural member.

5. The method set forth in claim 3 wherein the propagation velocity change measurement is made by detecting changes in optical path length between a detector of the pulsed beam and a point on a surface of the structural member, but removed from the point at which pulsed beam is directed onto the surface.

6. A system for measuring local elastic stress in a fastener hole of a structural member comprising:
   means for introducing ultrasonic energy into the member during cold working the hole;
   means for measuring the propagation velocity changes of the energy as the hole is cold worked;
   wherein the cold working is terminated when a preselected propagation velocity is measured corresponding to optimum induced elastic stress in the material around the hole.

7. A system as set forth in claim 6 wherein the ultrasonic energy is introduced by a piezoelectric transducer in contact with the structural member.

8. A system as set forth in claim 6 wherein the ultrasonic energy is introduced by a laser transducer removed from the structural member and directing a pulsed beam of light toward a surface of the structural member.

9. A system as set forth in claim 7 wherein the means for measuring the propagation velocity changes of the energy as the hole is cold worked includes an ultrasonic piezoelectric detector positioned in contact with the structural member.

10. A system as set forth in claim 8 wherein the means for measuring the propagation velocity changes of the energy as the hole is cold worked includes a detector, located at a distance from the structural member, for measuring changes in optical path length between the detector and a point on a surface of the structural member, but removed from a point at which the pulsed beam is directed onto the surface.

* * * * *